United States Patent [19]

Jizomoto et al.

[11] Patent Number: 5,480,655
[45] Date of Patent: Jan. 2, 1996

[54] PROCESS FOR PREPARING NONCOHESIVE COATING LAYER

[75] Inventors: Hiroaki Jizomoto, Ibaraki; Koichiro Hirano, Hyogo; Eri Kanaoka, Osaka, all of Japan

[73] Assignee: Shionogi Seiyaku Kabushiki Kaisha, Osaka, Japan

[21] Appl. No.: 13,538

[22] Filed: Jan. 28, 1993

Related U.S. Application Data

[63] Continuation of Ser. No. 725,670, Jul. 3, 1991, abandoned.

[30] Foreign Application Priority Data

Aug. 31, 1990 [JP] Japan ..................................... 2-230185

[51] Int. Cl.$^6$ .............................. A61K 9/50; B01J 13/10; B01J 13/22
[52] U.S. Cl. .......................... 424/492; 264/4.3; 264/4.32; 264/4.33; 428/402.2; 514/821
[58] Field of Search .................................... 264/4.3, 4.32, 264/4.33; 428/402.2; 427/213.31, 213.32, 213, 35, 3, 214, 2.14, 2.21; 424/492; 514/821

[56] References Cited

U.S. PATENT DOCUMENTS

| | | | |
|---|---|---|---|
| 3,137,630 | 6/1964 | Hecker et al. | 264/14 |
| 3,179,600 | 4/1965 | Brockett | 264/433 X |
| 4,268,411 | 5/1981 | Iwata et al. | 428/402.22 |
| 4,464,317 | 8/1984 | Thies et al. | 264/4.3 |
| 4,479,911 | 10/1984 | Fong | 427/3 |
| 4,703,051 | 10/1987 | Adachi et al. | 514/291 |
| 4,966,770 | 10/1990 | Giannini et al. | 424/493 |
| 5,013,557 | 5/1991 | Tai | 427/3 |

FOREIGN PATENT DOCUMENTS

| | | | |
|---|---|---|---|
| 0039441A2 | 11/1981 | European Pat. Off. | |
| 1560290 | 3/1969 | France. | |
| 1188957 | 4/1970 | United Kingdom | 424/492 |

OTHER PUBLICATIONS

Palmieri, Journal of Pharmaceutical Sciences, vol. 68, No. 12, Dec. 1979, pp. 1561–1562.
Takenaka et al., Journal of Pharmaceutical Science, vol. 69, No. 5, May 1980 pp. 513–516.
Deasy, Marcel Dekker, 1984, pp. 64–81, 89–95.
Ajinomoto et al., Patent Abstracts of Japan, vol. 8, No. 122 (C–227) (1559) Jun. 8, 1984.

*Primary Examiner*—Richard D. Lovering
*Attorney, Agent, or Firm*—Wenderoth, Lind & Ponack

[57] ABSTRACT

A process for producing microcapsules with an adhesive coating layer which comprises forming a slurry of microcapsules in a medium selected from water, one or more organic solvents or a mixture thereof by a coacervation method, adding powders of a pharmaceutically acceptable inorganic compound which is insoluble in the medium to the slurry, so that the inorganic compound adheres to substantially the overall surface of the adhesive coating layer, and separating the microcapsules from the medium.

6 Claims, 3 Drawing Sheets

PROCESS FOR PREPARING NONCOHESIVE COATING LAYER

This application is a continuation of now abandoned application Ser. No. 07/725,670, filed on Jul. 3, 1991 abandoned.

BACKGROUND OF THE INVENTION

1. Field of the Invention

The present invention relates to a process for preparing a non-cohesive coating layer useful in the production of microcapsules, a process for the production of the microcapsules comprising said process for preparing a noncohesive coating layer, and microcapsules prepared by said process therefor. More particularly, it relates to microcapsules which are prepared from an emulsion and may advantageously regenerate an emulsion in the living body. Such microcapsules are useful in the fields of pharmaceuticals, cosmetics and foods.

Microcapsules are very small particles or drops of solid, liquid, solution or suspension encapsulated in a coating layer of high molecular compounds. Recently, microcapsules have attracted considerable attention as a means for producing a solid preparation from a liquid active substance and as a means for producing a preparation which is stable to the surroundings from a substance which is unstable.

2. Discussion of Prior Art

The known process for the production of microcapsules is classified into (1) a mechanical or a physical process and (2) a chemical or a physicochemical process, in which a physicochemical process involving coacervate formation is known as the coacervation method. The latter method comprises three steps, i.e. (1) preparation of an adhesive coating layer by forming a coacervate phase, (2) stabilizing (or hardening) of the coating layer and (3) recovering powders (or drying). It is to be noted that, in the conventional process, the coating layer should be stabilized before recovering and the stabilization has been usually attained by hardening.

The conventional methods of hardening include physical treatment such as heating or cooling and treatment with chemicals such as formalin. Upon such treatment, the primarily formed sticky coating layer changes to a nonsticky insoluble matter which, however, is difficult to be disintegrated under such mild conditions as in a living body, and is difficult to quickly release its contents. Moreover, since the above hardening treatment takes a considerable time and results in undesirable remaining of chemicals used in hardening which may cause problems, the hardening procedure has been a bottleneck of the process for producing microcapsules by the coacervation methods.

Japanese Patent Publication (unexamined) No. 36540/1984 discloses a process for production of microcapsules which comprises recovering microcapsules in the form of powders without partial or complete hardening of a coating layer.

In this case, while the stabilizing step (2) may certainly be omitted, a great amount of powders such as starch is required to add as a powdering agent to a slurry of microcapsules following removal of a medium in which the coacervation is occurred. Moreover, when the thus obtained microcapsules are subjected to steps of drying and sieving out of the powdering agent to give powdery microcapsules, microcapsules thus prepared are not uniform in size and the microcapsules are not sufficiently fluidic. Thus the above mentioned method is disadvantageous in practical use.

As the result of an extensive study to overcome the above drawbacks and problems in the known coacervation method, it has now been discovered that when a certain kind of inorganic compound is used as a powdering agent, noncohesive and sufficiently fluidic microcapsules can be obtained without the stabilizing (hardening) step (2).

SUMMARY OF THE INVENTION

The present invention provides a process for preparing a noncohesive coating layer on microcapsules, which comprises adding powders of a pharmaceutically acceptable inorganic compound which is insoluble in a medium selected from water, one or more organic solvents or a mixture thereof, to a slurry of microcapsules with an adhesive coating layer in said medium, so that said inorganic compound adheres to substantially the overall surface of said adhesive coating layer. The invention also provides a process for producing microcapsules with an adhesive coating layer which comprises forming a slurry of microcapsules in a medium selected from water, one or more organic solvents or a mixture thereof by a coacervation method, adding powders of a pharmaceutically acceptable inorganic compound which is insoluble in said medium to said slurry, so that said inorganic compound adheres to substantially the overall surface of said adhesive coating layer of microcapsules and separating the microcapsules from said medium, and microcapsules prepared by said process for the production of microcapsules.

DETAILED DESCRIPTION OF THE INVENTION

Figure 1:
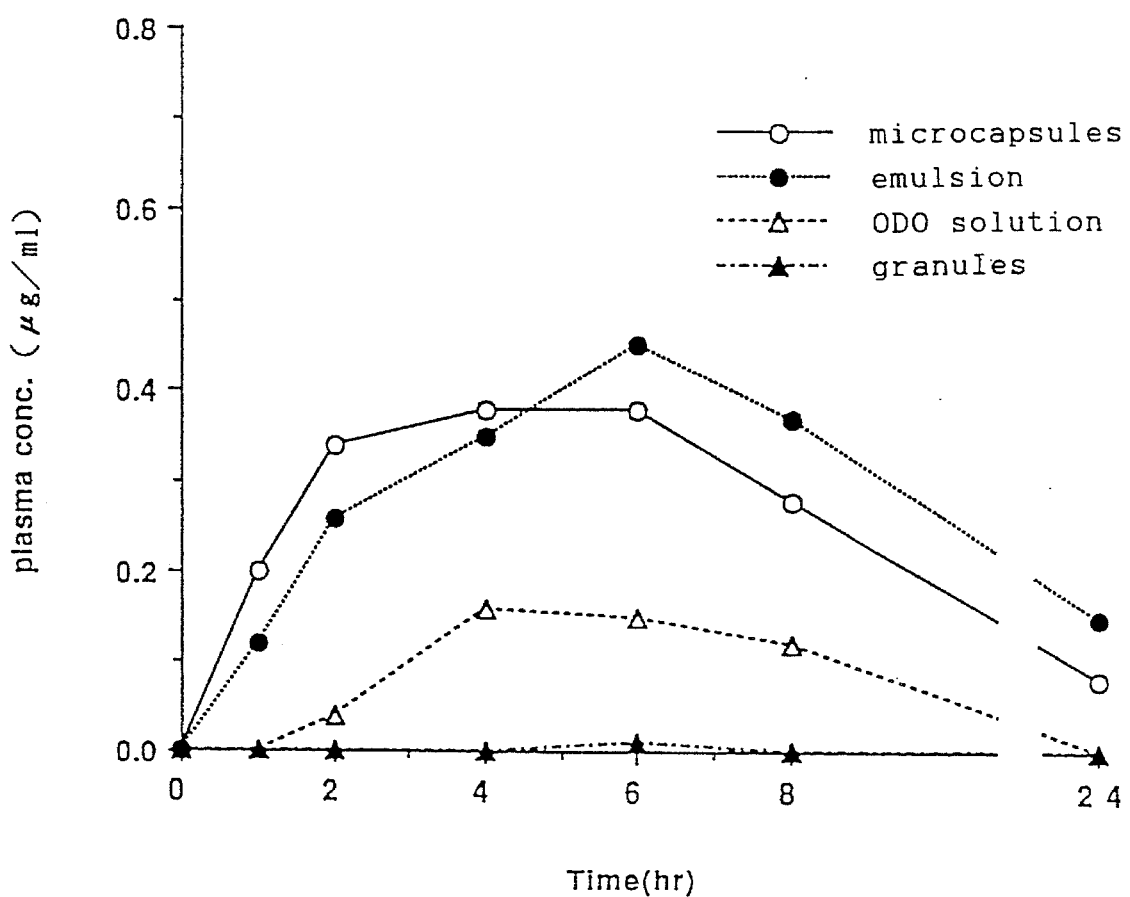
FIG. 1 shows the change in concentration of Probucol in blood plasma of rats with fasting as a function of time elapsed.

Inorganic compounds used in this invention are those insoluble in the medium in which microcapsules are formed. Such medium includes water, one or more organic solvents and a mixture thereof. The term "insoluble" means completely or substantially (or practically) insoluble and the latter includes hardly soluble, for example, having a solubility less than 1 g/1000 ml or 1 g/10000 ml. These compounds should be pharmaceutically acceptable, for example, non toxic. Specific examples of the inorganic compounds are inorganic oxides such as silica (silicon dioxide), inorganic hydroxide such as aluminium hydroxide, salts such as aluminium, calcium, magnesium salts of inorganic acids, for example, magnesium metasilicate aluminate, calcium carbonate, calcium phosphate, and among them, silicon containing compounds such as silica is the most preferred.

The powders should have a mean particle size of from about 0.01 to about 10 μm, preferably from about 0.05 to 5 μm, and most preferably from about 0.01 to about 1 μm. The powders may be used in such an amount as from about 1 to 100% by weight, preferably from about 5 to about 50% by weight based on the substance used as a coating material. The inorganic compound should be added to an extent to form a noncohesive coating layer.

Further, if desired, the present invention is also accomplished by partly hardening the coating layer of microcapsules with a hardening agent conventionally used such as tannic acid, potassium alum (aluminium potassium sulfate), and then by adding a relatively small amount of an inorganic compound used in this invention to said microcapsules.

The powders of inorganic compounds may be added to the medium at either stage before or after forming the coating layer or at both stages.

The process for preparing a noncohesive coating layer on microcapsules according to the present invention may take the place of the processes for the production of microcapsules which include a stabilizing (hardening) step of the coating layer such as the process which comprises forming the coating layer, hardening the layer and drying. In view of the characteristic nature of the process, the coacervation method herein includes not only the process in which the coacervate phase is formed in an aqueous medium, such as that represented by the complex coacervation method, but also other processes such as the process in which the coacervate phase is formed in an organic medium such as acetone, methylethylketone, etc., in a method using a combination of high molecular substance/solubilizing solvent/ liquid polymer for separating phase, the (pH-control) process in which solubility of polymer in a aqueous solution is decreased by controlling pH in order to form a coacervate phase, and the secondary emulsion process (interfacial precipitation process) in which coacervate formation is effected by interfacially precipitating from complex coacervate by removing the solvent. Further, microcapsules with noncohesive coating layer in this invention may be microspheres or microbeads comprising gelatin or other polymers and formed from w/o or w/o/w type emulsion using a drying-in-liquid method.

According to the present invention, after adding powders of an inorganic compound, such as silica powders, to a medium containing microcapsules with an unhardeed coating layer and allowing such powders to adhere to substantially the overall surface of the coating layer, noncohesive, uniform powders of microcapsules with good fluidity are obtained by removal of the medium by the conventional drying procedure. The drying step is advantageously carried out by the conventionally used procedures avoiding disintegration of microcapsules by a high temperature, such as removal of moisture by filtration, centrifugation or decantation, followed by dehydration using a lower alkanol such as isopropanol, freeze-drying or spray drying.

Any substance capable of being liquid can be used as a core substance of microcapsules. When said substance is an oily substance, it may be used as such, and when it, being crystalline or non-crystalline, is insoluble or difficultly soluble in water, it may be used in a form of solution or a suspension in an appropriate oil. For use of pharmaceuticals, any substance which meets all the above requirements can be used. This includes, for example, Vitamins such as Vitamin A, D, E or K, Prostaglandins, antibiotics, antiinflammatory agents, hypotensives, steroids, antitumor agents or anti-arterial-sclerosis agents, etc. Examples of the appropriate oil are sesame oil, soybean oil, liquid paraffin, medium chained fatty acid triglyceride such as migliol, ODO.

As the coacervate forming material, gelatin alone or gelatin and acacia are preferred, but other conventional coacervate forming materials may also be used, such as sodium alginate, propylene glycol alginate, carrageenan, agar, tragacanth, carboxymethylcellulose, aminoalkyl methacrylate copolymer, carboxyvinyl polymer, polyvinyl acetal diethylamino acetate, carboxymethylethylcellulose, styrene maleic acid copolymer, sodium polyvinyl sulfonate, polyvinyl acetate, cellulose acetate butyrate, benzyl cellulose, ethyl cellulose, polyethylene, polystyrene, natural rubber, nitrocellulose, ketone resin, polymethyl methacrylate, polyamide resin, acrylonitrile-styrene copolymer, epoxy resin, vinylidene chloride-acrylonitrile copolymer, polyvinyl-formal, cellulose acetate, hydroxypropyl cellulose, hydroxypropylmethyl cellulose, hydroxymethylcellulose acetate succinate, vinyl chloridevinyl acetate copolymer, polyvinyl chloride, shellac, polyester, polycarbonate, cellulose acetate propionate, polyvinyl pyrrolidone, hydroxypropylmethylcellulose phthalate, methacrylate copolymer, cellulose acetate phthalate, phenylsiloxane ladder polymer, polylactic acid, polyglycolic acid, polylactic acid glycolic acid copolymer, polyglutamic acid and polylysine.

The process of the present invention can eliminate not only the hardening step in the process for forming microcapsule spheres but also the resuspending step in the drying process.

Further, it has been found that the microcapsules according to the invention can more advantageously regenerate an emulsion than the conventional formulations as shown by the results obtained in the following Test Example with appendant FIGS. 1 to 3.

Practical embodiments of the invention are illustratively shown in the following non-limiting Examples.

EXAMPLE 1

Tocopheryl acetate (30 g) was added to a solution of gelatin (10 g in 340 ml purified water) in a beaker (1 liter) at about 50° C. and they were mixed together by a Silverson type homogenizer to make an emulsion mixture. To the emulsion was then added a solution of acacia (10 g in 340 ml in purified water) previously warmed at 50° C., and the mixture was adjusted to pH about 4 by adding 5% aqueous acetic acid solution under sufficient stirring. The emulsion was stirred and cooled slowly, during which white carbon (Carplex #80, Shionogi Co., Ltd.; 4 g) was added. When the mixture was cooled to a temperature below 10° C., stirring was stopped. The obtained slurry of microcapsules was dehydrated with 1 liter of isopropanol, and the dehydrated microcapsules were dried on a filter paper at room temperature for 2 days.

As the result, powdery microcapsules having a particle size of 100 to 200µm were obtained which were noncohesive and had excellent fluidity.

EXAMPLE 2

In the same manner as in Example 1 but using ODO, a kind of triglyceride, instead of tocopheryl acetate, and using white carbon (Siroid 244, Fuji Devison Co., Ltd.) instead of white carbon #80, there were produced unhardened microcapsules of which the coating layer consisted of gelatin and acacia, and the core substance is ODO.

EXAMPLE 3

In the same manner as in Example 1 but using Sudan III (46 mg/100 ml) in sesame oil (30 g) instead of tocopheryl acetate, there were produced similar unhardened microcapsules.

EXAMPLE 4

In the same manner as in Example 1 but using liquid paraffin instead of tocopheryl acetate, there produced unhardened microcapsules having an adhesive coating layer consisting of gelatin and acacia. After forming the coacervate phase as above, the mixture was stirred and cooled to a temperature below about 10° C., and the stirring was stopped. The supernatant was then removed from the mixture, and 5% tannic acid solution (500 ml) was added to the residue containing microcapsules. The mixture was stirred for 20 minutes. The mixture was then washed with water two times by decantation and white carbon (Carplex #80, 4 g) was added to the obtained slurry of microcapsules. Then the slurry was dehydrated using isopropanol as described in Example 1.

EXAMPLE 5

A slurry of microcapsules was prepared by treating the residue consisting of coacervate with 5% tannic acid solution and washing with water in the same manner as in Example 4. To the slurry (175 ml; content of microcapsules: about 100 ml) was added white carbon (Carplex #80) (1.5 g), and the mixture was subjected to spray drying (Yamato, Minispray model DL-21) to form powders.

EXAMPLE 6

Probucol (4,4'-[1-Methylethylidene-di(thio)]bis[2,6-bis(1,1'-dimethylethyl)phenol]) (4 g) was dissolved in ODO (30 g), and the solution was added to a solution of gelatin (Miyagi Kagaku Kogyo; 10 g in 340 ml purified water) previously warmed at about 50° C. in a 1 liter beaker. The mixture was subjected to homogenization with Silverson Homogenizer. To the obtained emulsion was added a solution of acacia (10 g in 340 ml purified water) previously warmed at about 50° C. The mixtures was adjusted to about pH 4 by adding 5% aqueous acetic acid solution with stirring. Then the mixture was slowly cooled with stirring, during which white carbon (Carplex #80, Shionogi Co., Ltd.) (4 g) was added thereto. When the mixture was cooled to a temperature below 10° C., the stirring was stopped. The slurry of microcapsules thus obtained was dehydrated with 1 liter of isopropanol and then the dehydrated microcapsules were dried on a filter paper at room temperature for 2 days. The characteristics of the powdery microcapsules trapping Probucol thus obtained, which were used in the following Test Example 1, are shown in Table 1.

EXAMPLE 7

In the same manner as in Example 6, but using, instead of Probucol, 300 mg of S-312-d ((4s)-Methyl 4,7-dihydro-3-isobutyl-6-methyl-4-(3-nitrophenol)thieno-[2-,3-b]pyridine-5-carboxylate), a Ca blocker, there were produced powdery microcapsules trapping S-312-d without a hardening step. The characteristics of the obtained microcapsules are shown in Table 1.

TABLE 1

| | Core substance mg/gMC | Yield (%) | Particle size (μm) | bulk/ density (g/cc) | repose angle (deg.) |
|---|---|---|---|---|---|
| Probucol (Example 6) | 71.8 | 98 | 130–200 | 0.53 | 19 |
| S-312-d (Example 7) | 5.1 | 90 | 100–250 | 0.51 | 27 |

The microcapsules of the present invention were disintegrated in order to show that they can regenerate the emulsion.

The microcapsules obtained in Example 1 (500 mg) were added, with stirring at 37° C., to the 1st test solution (900 ml) and the 2nd test solution (900 ml) defined in the Japanese pharmacopeia XI, respectively. It was observed under an optical microscope that the coating layer was disintegrated within 3 minutes and the emulsion was regenerated.

The 1st test solution: Sodium chloride (2.0 g), diluted hydrochloride (24.0 ml) and water were mixed to give a total volume of 100 ml.

The 2nd test solution: 0.2M dipotassium hydrogen phosphate (250 ml) and 0.2N sodium hydroxide (118 mL) and water were mixed to give a total volume of 1000 ml.

From the above results, it can be understood that the microcapsules of the present invention may be advantageously administered orally as such or after providing with other functions, for example, enteric property, after filling in capsule shells, shaping as granules, microgranules, or compressing as tablets, and they can readily regenerate the emulsion in the gastrointestinal tract.

The bioavailability of the microcapsules according to the invention was studied using rats and beagle dogs with reference to other dosage forms.

Test Example 1

The microcapsules trapping Probucol obtained in Example 6 were orally administered to male Slc-Wistar rats aged 10 weeks which had been kept fasting overnight and similar rats which had been allowed free access to food and water (n=4 or 5). The absorption in the gastrointestinal tract was compared with that of other dosage forms, i.e. a ODO solution containing Probucol 42 mg/gODO, an O/W emulsion containing Probucol: 5.0% (w/w); ODO: 30% (w/w) and purified yolk lecithin: 3.6% (w/w), granules containing 50% (w/w) Probucol which were prepared by adding starch and lactose as fillers and polyoxyethylene sorbitan fatty acid ester and processing in the conventional manner. The conditions of the experiments are shown in Table 2. Samples of blood were drawn from candal veins of rats at 0, 1, 2, 4, 6, 8 and 24 hours after oral admistration under anesthesia with ether.

Results

Figure 2:
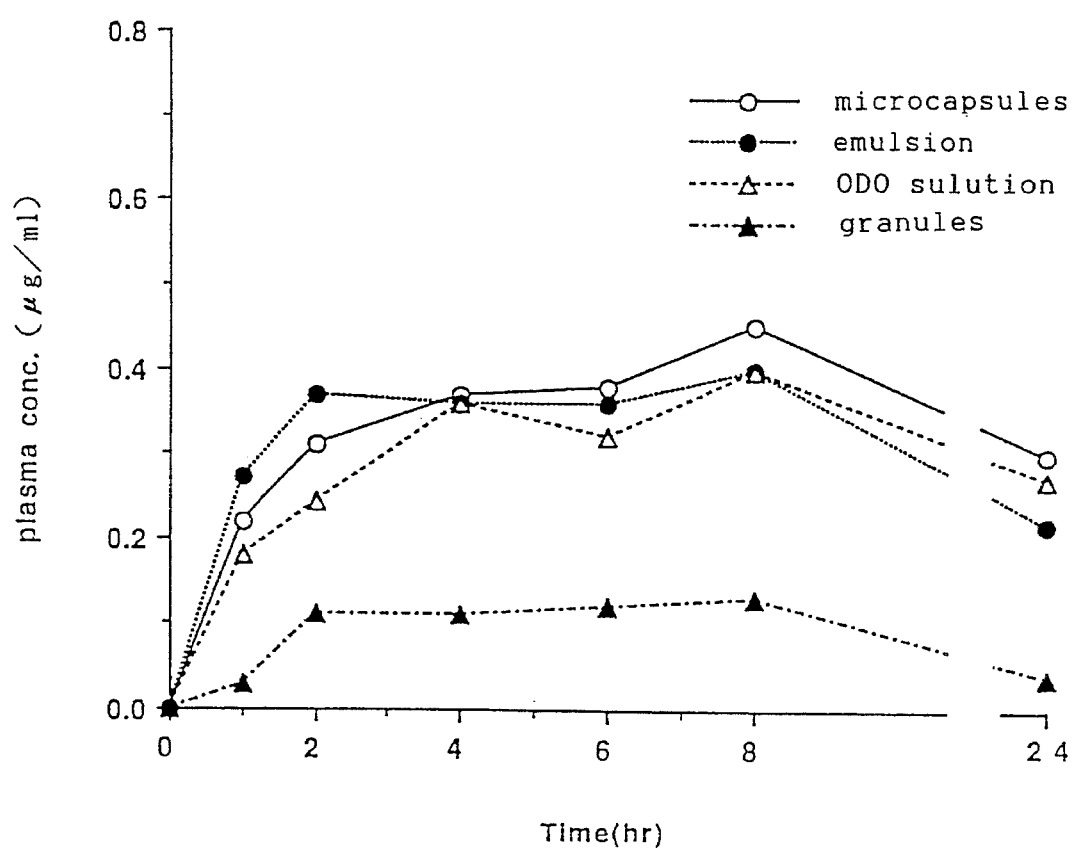
FIG. 2 shows the change in concentration of Probucol in blood plasma of rats without fasting as a function of time elapsed.

The results are shown in FIGS. 1 and 2. The microcapsules of the invention are remarkably more effective in availability than the granules, and more effective than the ODO solution under the conditions of fasting, and moreover the availability of microcapsules is as equal as that of the emulsion. These results indicate that the microcapsules regenerated the emulsion.

TABLE 2

| Oral administration of microcapsules trapping Probucol in rats | |
|---|---|
| The administration formulations | Probucol content |
| (1) microcapsules | 72 mg/g |
| (2) emulsion (O/W) | 14 mg/g |
| (3) ODO solution | 42 mg/g |
| (4) granules | 500 mg/g |

Male Slc-Wistar rats aged 10 weeks were used, which had been kept fasting or not fasting.

Each formulation was administered orally at a dose of 20 mg/kg as Probucol.

Under anesthesia with ether, the formulations dissolved in 1.0 ml of water were administered orally via a tube in Tests (1) and (4), and via an oral probe syringe in Tests (2) and (3).

Test Example 2

The microcapsules trapping S-312-d obtained in Example 7 were administered to male beagle dogs weighing 10.2kg which had been kept fasting for 24 hours (n=6). The absorption in the gastrointestinal tract was compared with other dosage forms, i.e. an ODO solution containing S-312-d 0.3 g/30 gODO, and powders diluted in 10 times lactose. All the S-312-d preparations were filled in capsules and administered at a dose of 10 mg/animal.

Results

Figure 3:
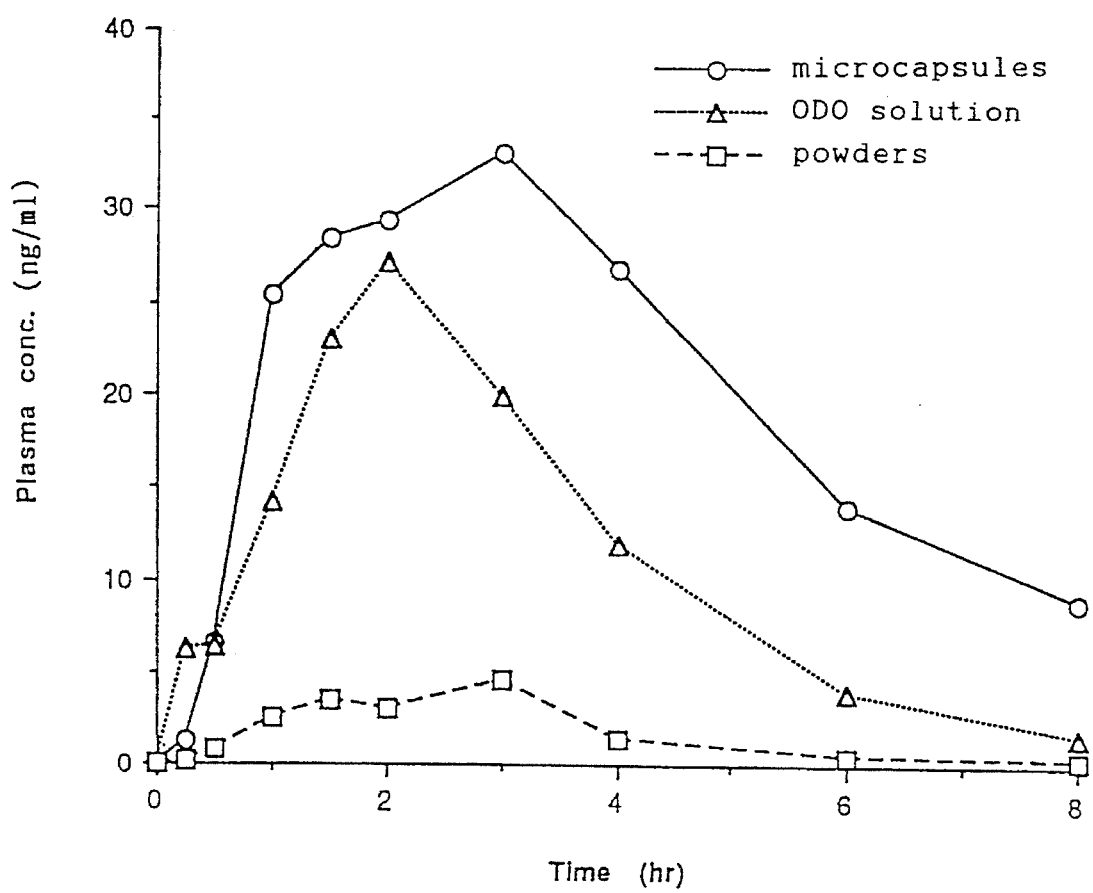
FIG. 3 shows the change in concentration of S-312-d in blood plasma of beagle dogs with fasting as a function of time elapsed.

The results are shown in FIG. 3. The microcapsules of the invention are remarkably more effective in availability than the powders, and more effective than the ODO solution.

What is claimed is:

1. A process for preparing microcapsules each having a noncohesive coating layer at the surface, which comprises
   (a) forming a slurry of microcapsules in water by coacervation, said microcapsules each comprising a pharmaceutical substance in a liquid or solution state as the core and an adhesive coating layer of a coating material at the surface,
   (b) adding a pharmaceutically acceptable inorganic substance insoluble in said water to said slurry, the amount of the inorganic substance being from 1 to 100% by weight based on the weight of the coating material in the adhesive coating layer, to form a noncohesive coating layer of the inorganic substance at the surface of each of the microcapsules,
   (c) recovering the microcapsules having a noncohesive coating layer from the slurry without previous addition of any hardening agent thereto, and
   (d) drying the recovered microcapsules to prepare microcapsules which are fluidic and of uniform size.

2. The process according to claim 1, wherein the coating material is gelatin or gelatin and acacia.

3. The process according to claim 1, wherein the inorganic substance is silica.

4. The process according to claim 1, wherein the coacervation is accomplished by addition of an acid to an emulsion of the pharmaceutical substance in an aqueous solution of a coating material.

5. The process according to claim 4, wherein the acid is acetic acid.

6. The process according to claim 1, wherein the pharmaceutical substance is (4s)-methyl 4,7-dihydro-3-isobutyl-6-methyl-4-(3-nitrophenol)thieno-[2,3-b]pyridine-5-carboyxlate.

* * * * *